United States Patent [19]

Vickers

[11] 4,070,408
[45] Jan. 24, 1978

[54] AROMATICS EXTRACTION AND DISTILLATION PROCESS

[75] Inventor: Anthony G. Vickers, Arlington Heights, Ill.

[73] Assignee: UOP Inc., Des Plaines, Ill.

[21] Appl. No.: 702,832

[22] Filed: July 6, 1976

[51] Int. Cl.$^2$ ............................................... C07C 3/58
[52] U.S. Cl. ............................ 260/672 R; 203/69; 203/99; 203/DIG. 9
[58] Field of Search ...... 260/672 R, 674 SA, 674 SE; 203/69, 98, 99, DIG. 9

[56] References Cited

U.S. PATENT DOCUMENTS

| | | | |
|---|---|---|---|
| 3,204,006 | 8/1965 | Broughton | 260/672 R |
| 3,204,007 | 8/1965 | Mukai et al. | 260/672 R |
| 3,996,305 | 12/1976 | Berger | 260/674 SE |

Primary Examiner—O. R. Vertiz
Assistant Examiner—Brian E. Hearn
Attorney, Agent, or Firm—James R. Hoatson, Jr.; Richard D. Stone; William H. Page, II

[57] ABSTRACT

An improved aromatics extraction process is disclosed. Key feature of the present invention is use of the fractionator in the hydrodealkylation unit or other unit with a benzene fraction to fractionate not only hydrodealkylated benzene but also extracted benzene. The extracted benzene is used as "pseudo" reflux in the hydrodealkylation unit fractionator, thereby reducing the reflux requirement. The conventional re-run fractionator for clay treated benzene extract is eliminated, since polymerized olefins in this extract are removed as a bottoms fraction from the hydrodealkylation fractionator.

17 Claims, 1 Drawing Figure

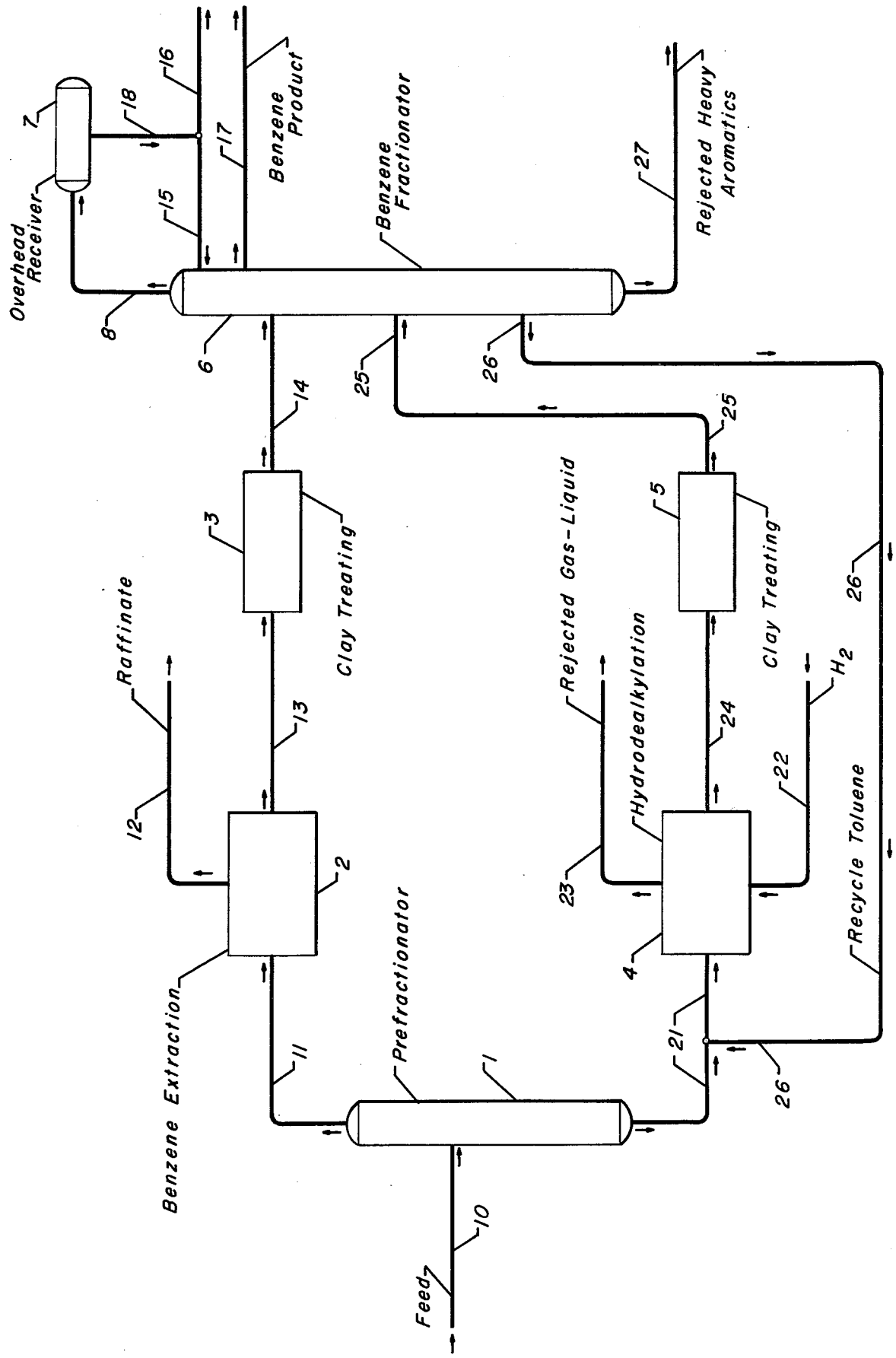

4,070,408

AROMATICS EXTRACTION AND DISTILLATION PROCESS

BACKGROUND OF THE INVENTION

1. Field of the Invention

The present invention relates to an improved combination process. The processes are hydrodealkylation of toluene, or toluene and heavier aromatics, and extraction of benzene. Extracted benzene is used to satisfy part of the reflux requirement of the hydrodealkylation unit product fractionator. The inventive concept may also be used when a benzene extraction unit is added to a refinery with an existing benzene fractionator, e.g., an existing aromatics extraction unit with a feed of benzene, toluene and xylenes.

The invention is specifically described with reference to thermal hydrodealkylation of a toluene fraction, and extraction of benzene from non-aromatics in an extraction unit using Sulfolane solvent.

2. Description of the Prior Art

Hydrodealkylation (HDA) of toluene and heavier alkylaromatics to benzene is a well known process. In a typical dealkylation unit, toluene is contacted with hydrogen, perhaps in the presence of a catalyst, at high temperature to remove the methyl group from the toluene feed, thereby producing benzene. An excellent overall view of this process is presented in Kirk-Othmer, *Encyclcopedia of Chemical Technology*, Second Edition, Inter-Science Publishers, N.Y., 1966, Volume 11, page 453, entitled "Hydrodealkylation." The teachings of this article are incorporated by reference.

Typically, less than 100% conversion of the feed to desired product occurs in the reaction zone, so a fractionator is usually provided to separate benzene from unconverted toluene to permit recycle thereof to the reaction zone. It is also conventional in many units, to provide clay treating of the feed to the dealkylation unit fractionator. The purpose of clay treating is to remove trace amounts, typically 10 to 5000 wt ppm, of olefins present in the dealkylation effluent. Clay treating polymerizes these olefins and permits their removal from the benzene product by fractionation. It is not possible to simply clay treat the benzene product after fractionation because, although the olefins would be polymerized, the polymer would still be present in the benzene and would seriously degrade the color of the benzene product, necessitating further fractionation to remove polymers.

Examples of typical dealkylation units are given in U.S. Pat. Nos. 3,204,007 and 3,204,006, both in Class 260-672. The teachings of these patents are incorporated by reference. U.S. Pat. No. 3,204,007 discloses a dealkylation unit wherein reactor effluent passes through heat exchangers and coolers into a vapor-liquid separator. The liquid fraction is clay treated and then fractionated to produce benzene product and toluene for recycle.

U.S. Pat. No. 3,204,006 discloses a dealkylation unit with feed pretreatment facilities which permit desulfurization of the feed in a hydrorefining zone, and also removal of nonaromatics from the feed. In this patent, it is contemplated that the product fractionator will also fractionate a feedstock containing some aromatics. To the extent that this patent provides for fractionation of mixtures of reactor effluent and outside benzenes in a single fractionation column, the treatment of these streams in the distillation column is as a gross mixture thereof.

Aromatics extraction is also a very old process. Typically these units separate a catalytic reformate or a coke oven light oil, via liquid-liquid extraction or extractive distillation or both, into aromatics and non-aromatics. The development of one commercial process has been reported at the 7th World Petroleum Congress, Volume IV, pages 65-73, 1967, which article is incorporated by reference.

In the past it was customary to treat a feed in an aromatics extraction unit which contained not only benzene but also toluene and xylenes and perhaps heavier aromatics as well. With the trend toward higher severity reforming, the amount of non-aromatics which survive the reforming zone has diminished. Recently, the amount of non-aromatics boiling in the toluene and xylene fractions has been low enough to permit the toluene fraction to be fed directly to a hydrodealkylation unit, and the $C_8$ aromatics to be fed directly to conventional xylene extraction and separation processes, all without aromatics extraction. Typically, non-aromatic content of the $C_7$ fraction will be less than 10%, preferably less than 5%. Accordingly, the need for aromatics extraction capacity treating feeds heavier than benzene has seriously diminished. Many refiners require aromatics extraction of only the benzene fraction from a reformate. Unfortunately, the benzene product obtained from such a specialized extraction unit, although fairly pure, still requires expensive fractionation downstream of the extraction unit.

Fractionation is required because the benzene product from the aromatics extraction unit is inevitably contaminated with trace amounts of olefins. These contaminants, if not removed, would cause the benzene to fail typical acid wash color tests, e.g., ASTM D-848. The traditional way of removing these contaminants is to pass the benzene product over a bed of clay, which polymerizes the olefins and permits their separation from benzene by fractionation. This is a relatively simple fractionation, because there is a great difference in boiling point between benzene and polymer. However, a substantial investment is required in even a simple fractionation column, and in addition to the reflux requirement, the entire benzene product must be vaporized and this increases the utility costs, as is well known by those skilled in the aromatics extraction art.

SUMMARY OF THE INVENTION

I have now discovered a way to interconnect two processes, hydrodealkylation or other unit with a benzene fractionator and a benzene extraction unit, and improve the operation of each process, while substantially reducing the capital expenditure and operating costs of both processes.

Accordingly, the present invention provides in a process for the fractionation of benzene in a benzene product fractionator wherein a benzene-rich stream is fed to an intermediate locus, benzene reflux is supplied to the top of the fractionator and benzene product is recovered from an upper portion of the fractionator, above the feed locus, material heavier than benzene is recovered from a lower portion of the fractionator, the improvement which comprises supplying as at least a portion of the reflux requirement of the benzene fractionator a high purity, clay treated benzene fraction derived from an aromatics extraction unit, wherein the extracted, clay treated benzene is added to the benzene fractionator at a point between the benzene product withdrawal locus, and the feed locus of the fractionator.

In a more limited embodiment, the present invention provides in a process for the hydrodealkylation of alkylaromatics to benzene where a stream comprising toluene is charged to a hydrodealkylation zone to produce a benzene and toluene-rich dealkylation effluent, containing trace amounts of olefins, the dealkylation effluent is passed through a clay treating zone for conversion of olefins to di-olefins, clay treated dealkylation effluent is introduced into an intermediate locus of benzene product fractionator wherein benzene reflux is supplied to the top of the fractionator and benzene product is recovered from an upper portion of the fractionator, above the feed locus, a toluene fraction is recovered from a lower portion of the fractionator for recycle to the hydrodealkylation unit, and heavy aromatics and polymerized olefins are removed as a bottoms fraction, the improvement which comprises supplying as at least a portion of the reflux requirement of the benzene fractionator a high purity, clay treated benzene fraction derived from an aromatics extraction unit, wherein the extracted, clay treated benzene is added to the benzene fractionator at a point between the benzene product withdrawal locus and the feed locus of the fractionator.

In another limited embodiment, the present invention provides a combination aromatics extraction and dealkylation process comprising: (a) extracting benzene from a benzene-rich fraction; (b) passing at least a portion of the extracted benzene through a first clay treating zone; (c) introducing clay treated benzene into a benzene fractionator at a first locus, in an upper portion thereof; (d) dealkylating a toluene-rich fraction to produce a benzene- and toluene-rich dealkylation effluent; (e) passing at least a portion of the dealkylation effluent through a second clay treating zone; (f) introducing clay treated dealkylation effluent into the benzene fractionator at a second locus, below said first locus; and, (g) withdrawing a benzene product from the benzene fractionator at a third locus above said first locus.

The essence of the present invention is the discovery that the clay treated product from a benzene extraction unit can be used as "pseudo reflux" in the benzene fractionator in a hydrodealkylation unit or other unit with a benzene fractionator to eliminate the necessity for a re-run column in the aromatics extraction unit.

The invention works well because the benzene product from the aromatics extraction unit contains only trace amounts of contaminants, the main offenders being 20–2000 wt ppm olefins before clay treating. These contaminants are present in amounts sufficient to make the benzene product "off specification." After clay treating, the olefin content is less than about 5 or 10 wt ppm, which is a common specification. The olefins are converted into polymer, and some of this polymer is adsorbed by the clay, but most is dissolved in the benzene. Thus, the net effect of clay treating is to convert one contaminant into another, however, the polymer is readily separable from the benzene by fractionation, while the olefin is not. Benzene purity, both before and after clay treating, is generally more than 99 mole percent.

I have determined that this material is pure enough to use as benzene reflux in the hydrodealkylation unit product fractionator, which separates benzene from recycled toluene. To avoid contamination of benzene product with polymer, the clay treated benzene extract is preferably added several trays below the benzene product withdrawal tray, to satisfy some of the reflux requirements of the benzene column. The separation of polymer from benzene is relatively simple, and can be accomplished in just a few trays of the benzene column.

The clay treated benzene extract is also suitable for use as pseudo reflux in any other benzene product fractionator which might exist in a refinery or petrochemical plant. Thus, if a refiner had an existing BTX aromatics extraction unit, it would include product fractionation facilities for benzene, toluene, and xylene. It would be possible to use clay treated extracted benzene from a new benzene extraction unit as pseudo reflux in an existing benzene fractionator.

Such situations are likely to arise whenever a refinery adds additional capacity. Thus, a refiner might add a new high severity reformer and want to recover the benzene from the reformate. Rather than extend the capacity of an existing BTX aromatics extraction unit, the refiner may choose to put in an extraction unit which would only handle the benzene fraction of the reformate. The refiner could avoid the cost of a separate benzene product fractionator for this incremental benzene production by charging this incremental benzene, after clay treating, to his existing benzene product fractionator in the aromatic extraction unit.

From the above it is clear that the benefits of the present invention are not limited to a combination of hydrodealkylation and aromatics extraction, even though this appears at the present time to be the ideal combination and one which will occur in future refineries. However, use of clay treated extracted benzene as benzene reflux in other benzene product fractionators is also within the scope of the present invention.

In the operation of the present invention, it is essential that the clay treatment of the benzene extract be carried on separately from clay treatment of hydrodealkylation unit product. If the benzene extract and hydrodealkylation unit effluent were commingled either before or after clay treatment there would be a significant increase in the work required of the benzene fractionator. This is because the benzene from the benzene extraction unit is almost pure. The prefractionator accomplished much work in generating this fairly pure benzene stream. This work of the prefractionator would be lost if pure benzene extract were mixed with the benzene and toluene mixture produced by the hydrodealkylation unit. Similarly, if one were to attempt to use the process of U.S. Pat. No. 3,204,006 to handle the relatively pure benzene, contaminated with only trace amounts of olefinic materials, there would be a significant increase in entropy of the system due to mixing of this pure extracted benzene with the benzene contained in the hydrodealkylation zone effluent. Thus, at best, this prior art suggests oversizing of the fractionator used to separate benzene from toluene. Oversizing the fractionator is not the present invention.

DESCRIPTION OF THE DRAWING

The present invention is illustrated with reference to the drawing which shows one preferred embodiment, wherein a hydrodealkylation unit is operated in conjunction with an aromatics extraction unit.

The drawing shows feed 10 entering prefractionator 1. Feed 10 is derived from a catalytic reformate. The reformer operates at high severity, so the non-aromatics content is less than 10 mole percent, preferably less than 5%, in the toluene fraction, or material boiling between 200 and 250° F. A benzene fraction is recovered overhead and charged via line 11 to benzene extraction unit 2. Non-aromatic material is rejected as a raffinate stream via line 12. The extract, which is a very pure benzene fraction contaminated with traces of olefins, is sent via line 13 to clay treating unit 3. The clay treated extract is charged via line 14 to product fractionator 6.

The bottoms fraction recovered from prefractionator 1 consists of toluene and any heavier material in the feed. This toluene fraction is charged via line 21, along with recycle toluene in line 26, to hydrodealkylation unit 4. Hydrogen is charged to the unit via line 22. A light gas and rejected liquid stream is removed from the hydrodealkylation unit via line 23. The benzene product of the hydrodealkylation unit, plus unconverted toluene, is charged via line 24 to clay treating unit 5. Clay treated hydrodealkylate is charged via line 25 to benzene fractionator 6.

Benzene fractionator 6, which receives both a relatively pure benzene extract via line 14 and a mixture of benzene and toluene via line 25, produces a pure benzene product as a side draw. As is typical in benzene fractionators the benzene product is not withdrawn as an overhead fraction, but rather is withdrawn about 2 to 10 trays, in this instance 4 trays, down the column as a side draw. There is an overhead fraction removed from fractionator 6 via line 8 which is cooled and collected in overhead receiver 7. Most of this steam is merely returned via line 15 to fractionator 6 as reflux. Strictly speaking, material returned via line 15 is both reflux and product, as product withdrawal occurs about four trays down, and material withdrawn in this manner does not satisfy the reflux requirement of the column. A small stream shown as line 16, is used to remove any accumulation of light materials which might accumulate in the process. The reflux required in fractionator 6 via line 15 is much less than that normally required in a product fractionator handling effluent from a hydrodealkylation unit. This is because the relatively pure benzene stream in line 14 supplies much of the reflux required in this column. Further, the combined internal reflux rate in the fractionator below the locus where the relatively pure benzene stream is introduced, is only that required for the separation of the hydrodealkylation benzene, whereas the sidecut benzene product also includes the benzene from extraction. To prevent any contamination of benzene product withdrawn via line 17, and to permit separation of polymerized olefins from benzene, the benzene extract enters 1 to 10 trays, or in this instance 4 trays, below the benzene product withdrawal point. This allows several stages of fractionation for separation of heavy polymer produced in clay-treating unit 3 from extracted benzene. Recycle toluene is withdrawn via line 26 for return to the hydrodealkylation unit. Heavy materials in the column are withdrawn via line 27.

ILLUSTRATIVE EMBODIMENT

A mole balance giving compositions of the streams influencing the fractionation is shown in Table I.

The reformate splitter, or prefractionator 1, contains 50 valve trays. The column internal diameter is 8 feet. The feed point is located in the middle of the column. Column pressure is 5 psig. at the top and 13 psig. at the bottom.

Hydrodealkylation unit 4 is a thermal-hydrodealkylation unit, of conventional design.

The solvent in the aromatics extraction unit is Sulfolane. Those skilled in the art will realize that other solvents could as well be used, e.g., mixed glycols or DMSO. A combination of liquid-liquid extraction and extractive distillation is used to extract benzene. Because of the narrow boiling range of the feed, extractive distillation alone may also be used.

TABLE I

|  | Line | Lb Moles/Hr. Of Benzene | BPSD |
|---|---|---|---|
| Feed | 10 | 377.58 | 8,008 |
| Hydrodealkylation Feed | 21 | 2.15 | 3,682 |
| Benzene Extraction Feed | 11 | 375.43 | 4,326 |
| Raffinate | 12 | 0.20 | 2,055 |
| Extract | 13 | 375.23 | 2,271 |
| Benzene Reflux | 15 | 1219.00 | 7,900 |
| Benzene From HDA | 25 | 494.85 | 4,017 |
| Toluene Recycle | 26 | 20.00 | 1,133 |
| Benzene Product | 17 | 850.08 | 5,150 |
| Rejected Heavy Aromatics | 27 | — | 10 |

Benzene product fractionator 6 consists of a vessel containing 63 trays. More details about the column are shown in Table II.

TABLE II

| COLUMN SECTION | Benzene Column | | |
|---|---|---|---|
|  | Top | Middle | Bottom |
| Operating Pressure, PSIG | 5 | 10 | 15 |
| Operating Temperature, ° F. | 195 | 285 | 415 |
| Column, I.D., Ft-In | 6-6 | 6-6 | 2-6 |
| Tangent Length, Ft-In | ← | 110-0 | → |
| Number of Decks | 38 | 20 | 5 |
| Feed Deck Number | — | 38 | — |
| Deck Spacing, Inches | 18 | 18 | 18 |
| Type of Deck | Sieve | Sieve | Sieve |
| Number of Liquid Flowpaths | 1 | 1 | 1 |

This HDA unit column is not made any larger to handle the clay treated benzene extract. The only modification to this column is the addition of a feed point at tray 9. Liquid loading in the column remains substantially the same, because reflux in line 15 is decreased to compensate for the inclusion of "pseudo reflux," in the form of clay treated benzene extract.

If the units are not combined with the use of extracted benzene as a "pseudo" reflux, as taught by the present invention, it will be necessary either to install a separate rerun column for benzene extract after clay treatment, or to mix the two feed streams ahead of the fractionator and install a significantly larger single fractionator. If a separate rerun column is installed, in addition to the investment cost associated with this column, the reboiler utility requirements will add about ⅓ to the utility requirement resulting from the practice of this invention. If the two feeds are mixed ahead of a common fractionator, the increase in utility requirement will be about ½ of that resulting from the practice of this invention.

I claim as my invention:

1. In a process for the fractionation of benzene in a benzene product fractionator wherein a benzene-rich stream is fed to an intermediate locus, benzene reflux is supplied to the top of the fractionator and benzene product is recovered from an upper portion of the fractionator, above the feed locus, and material heavier than benzene is recovered from a lower portion of the fractionator, the improvement which comprises supplying as at least a portion of the reflux requirement of the benzene fractionator a high purity, clay treated benzene fraction derived from an aromatics extraction unit, wherein the extracted, clay treated benzene is added to the benzene fractionator at a point between the benzene product withdrawal locus, and the feed locus of the fractionator.

2. Improved process of claim 1 wherein the extracted benzene prior to clay treating, contains 10 to 500 wt. ppm. olefin contaminants.

3. Improved process of claim 1 wherein the extracted, clay treated benzene has a mole purity of at least 99%.

4. Improved process of claim 1 wherein benzene is extracted with a solvent selected from the group of Sulfolane-type organic compounds and polyalkylene glycols.

5. In a process for the hydrodealkylation of alkylaromatics to benzene wherein a stream comprising toluene is charged to a hydrodealkylation zone to produce a benzene and toluene-rich dealkylation effluent containing trace amounts of olefins, the dealkylation effluent is passed through a clay treating zone for conversion of olefins to di-olefins, and heavier material, clay treated dealkylation effluent is introduced into an intermediate locus of benzene product fractionator wherein benzene reflux is supplied to the top of the fractionator and benzene product is recovered from an upper portion of the fractionator, above the feed locus, a toluene fraction is recovered from a lower portion of the fractionator for recycle to the hydrodealkylation unit, and heavy aromatics and polymerized olefins are removed as a bottoms fraction, the improvement which comprises: supplying as at least a portion of the reflux requirement of the benzene fractionator a high purity, clay treated benzene fraction derived from an aromatics extraction unit, wherein the extracted, clay treated benzene is added to the benzene fractionator at a point between the benzene product withdrawal locus and the feed locus of the fractionator.

6. The improved process of claim 5 wherein the feed to the hydrodealkylation unit and the feed to the benzene extraction unit are derived from a common prefractionator.

7. The improved process of claim 6 wherein the feed to the prefractionator is derived from effluent from a reforming unit operating at high severity so that the fraction of the reformate boiling in the benzene to xylene range contains less than 20 mole percent non-aromatic material.

8. A combination aromatics extraction and dealkylation process comprising:
 a. extracting benzene from a benzene-rich fraction;
 b. passing at least a portion of the extracted benzene through a first clay treating zone;
 c. introducing clay treated benzene into a benzene fractionator at a first locus, in an upper portion thereof;
 d. dealkylating a toluene-rich fraction to produce a benzene- and toluene-rich dealkylation effluent;
 e. passing at least a portion of the dealkylation effluent through a second clay treating zone;
 f. introducing clay treated dealkylation effluent into the benzene fractionator at a second locus, below said first locus; and,
 g. withdrawing a benzene product from the benzene fractionator at a third locus above said first locus.

9. The process of claim 8 wherein the extracted benzene and dealkylation effluent contain, prior to clay treating, 10 to 500 weight ppm olefin contaminants.

10. The process of claim 9 wherein the trace amounts of olefins in the extracted benzene and the dealkylation zone effluent are polymerized by the action of the first and second clay treaters and the polymer enters the benzene fractionator along with the clay treated extracted benzene and clay treated dealkylation effluent and the polymerized olefins are withdrawn from the benzene fractionator as a bottoms fraction.

11. The process of claim 8 wherein benzene reflux is provided in the benzene fractionator and the reflux enters the fractionator on the top tray, benzene product is withdrawn 2 to 10 trays below and extracted clay treated benzene enters the fractionator 1 to 10 trays below the benzene product tray.

12. The process of claim 8 wherein the extracted clay treated benzene has a mole purity of at least 99%.

13. The process of claim 8 wherein benzene is extracted with a solvent selected from the group of Sulfolane-type organic compounds and polyalkylene glycols.

14. The process of claim 8 wherein the dealkylation process is a thermal hydrodealkylation process operating in the presence of hydrogen.

15. The process of claim 8 wherein the hydrodealkylation process is a catalytic process operating in the presence of hydrogen.

16. The process of claim 8 wherein the benzene-rich fraction and the toluene-rich fraction are derived from a common prefractionator.

17. The process of claim 16 wherein the feed to the prefractionator is derived from effluent from a reforming unit operating at high severity characterized by a toluene fraction containing less than 10 mole percent non-aromatic material.

* * * * *